US006591135B2

(12) United States Patent  
Palmer et al.

(10) Patent No.: US 6,591,135 B2  
(45) Date of Patent: Jul. 8, 2003

(54) PORTABLE PATIENT MONITOR WITH DEFIBRILLATOR/PACEMAKER INTERFACE AND BATTERY POWER MANAGEMENT

(75) Inventors: Michael J. Palmer, New Berlin, WI (US); James M. Gray, Fox Point, WI (US); David L. Schieble, Oconomowoc, WI (US); Alan E. Clapp, Fox Point, WI (US); Brian Bayer, Menomonee Falls, WI (US); Wilfried Loehning, Horben (DE); Andreas Schulz, Bötzingen (DE); Horst Schlosser, Kenzingen (DE)

(73) Assignee: GE Medical Systems Information Technologies, Inc., Milwaukee, WI (US)

( * ) Notice: Subject to any disclaimer, the term of this patent is extended or adjusted under 35 U.S.C. 154(b) by 63 days.

(21) Appl. No.: 09/835,459

(22) Filed: Apr. 16, 2001

(65) Prior Publication Data

US 2003/0088275 A1 May 8, 2003

(51) Int. Cl.[7] .................................................. A61N 1/18
(52) U.S. Cl. .............................................. 607/5; 607/34
(58) Field of Search .............................. 600/509; 607/4, 607/5, 9, 33, 34, 61, 142

(56) References Cited

U.S. PATENT DOCUMENTS

| | | | | | |
|---|---|---|---|---|---|
| 3,865,101 | A | * | 2/1975 | Saper et al. | 128/2.06 R |
| 4,080,558 | A | * | 3/1978 | Sullivan | 320/39 |
| 4,096,856 | A | * | 6/1978 | Smith et al. | 128/4.19 D |
| 6,223,077 | B1 | * | 4/2001 | Schweizer et al. | 607/5 |
| 6,488,029 | B1 | * | 12/2002 | Hood et al. | 128/845 |

* cited by examiner

Primary Examiner—Kennedy Schaetzle  
Assistant Examiner—Frances P. Oropeza  
(74) Attorney, Agent, or Firm—Welsh & Katz, Ltd.

(57) ABSTRACT

A method and apparatus are provided for distributing power within a cardiac treatment and monitoring system which includes a defibrillator releasably coupled to a patient monitoring unit. The method includes the steps of determining a battery reserve capacity within the patient monitoring unit and distributing power from the patient monitoring system to a defibrillator when the determined battery reserve capacity exceeds a threshold value.

23 Claims, 4 Drawing Sheets

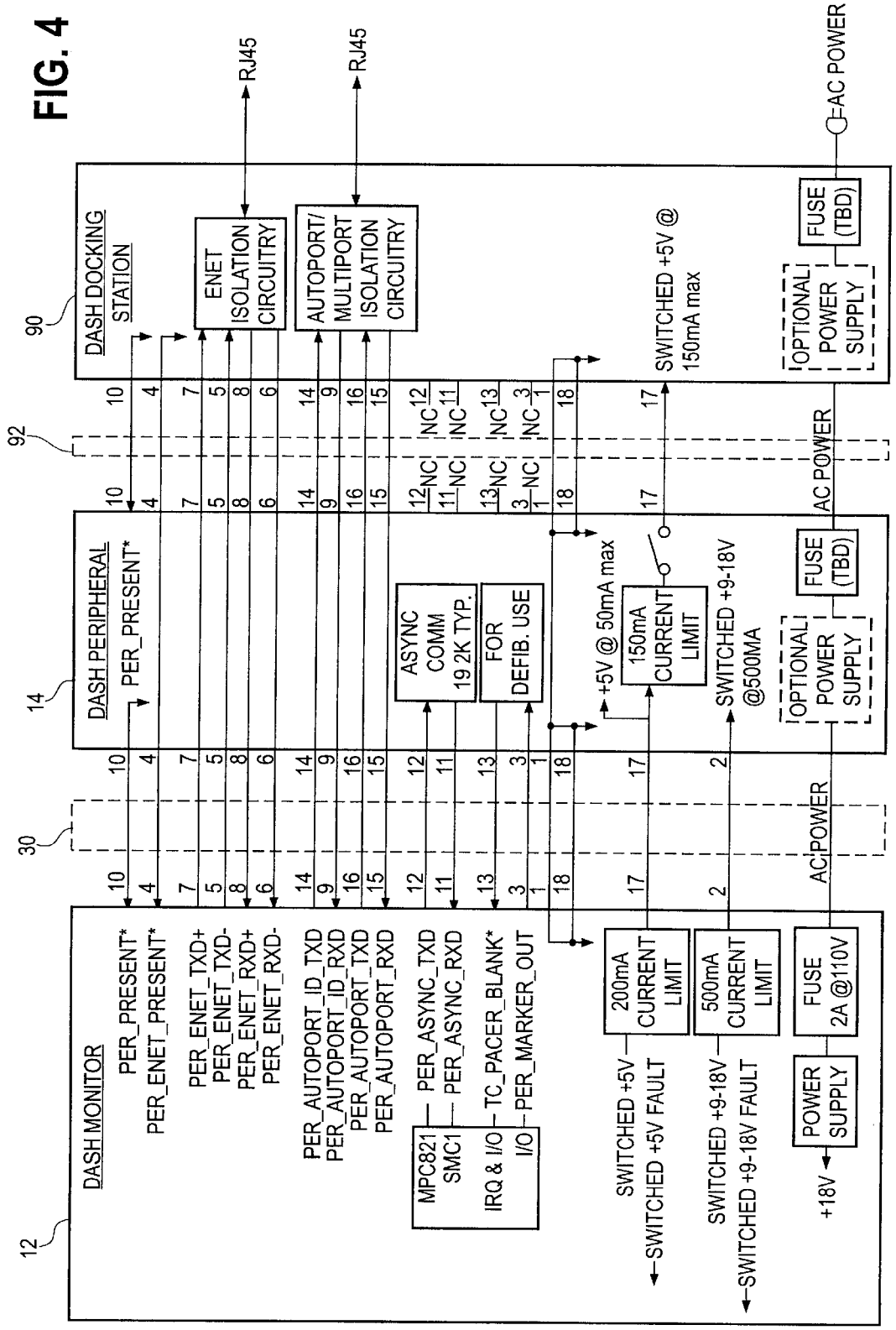

US 6,591,135 B2

PORTABLE PATIENT MONITOR WITH DEFIBRILLATOR/PACEMAKER INTERFACE AND BATTERY POWER MANAGEMENT

FIELD OF THE INVENTION

The field of the invention relates to cardiac defibrillation and more particularly to portable defibrillators and patient monitoring.

BACKGROUND OF THE INVENTION

Cardiac arrest can occur in humans for any of a number of reasons. Triggering events may include heart attack, accidental contact with high voltage sources or disease. While the term "cardiac arrest" suggests a total cessation of heart function, a more accurate characterization may be a lack of coordinated contractions among the various segments of the heart. The lack of coordinated contractions may be further characterized by the term "fibrillation". Often cardiac arrest may be reversed through application of an electric shock from a defibrillator.

Defibrillators have been constructed to operate under a number of different modes. Under a first mode, a defibrillator may deliver a one-time shock (usually in the case of full cardiac arrest) under control of an operator. Under other modes, the defibrillator may receive an R-marker from a heart monitor for other therapeutic processes (e.g., demand pacing, cardioversion, etc.).

The transport of critically ill patients may require the use of a cardiac monitor to monitor the patient's condition. In the case of the sudden onset of cardiac failure, it is often necessary to use defibrillators while transporting the patient (e.g., within a hospital, emergency vehicle, aircraft, etc.). Where used during transport, a defibrillator must rely upon battery power. However, batteries often deteriorate or become discharged during use. Because of the importance of defibrillators, a need exists for a more reliable method of supplying power to defibrillators during transport.

In addition, it is cumbersome to carry multiple instruments for cardiac monitoring and defibrillation. Further, users prefer not to carry more equipment than they need, therefore it is desirable to be able to separate defibrillator functions from monitoring functions.

SUMMARY

A method and apparatus are provided for distributing power within a cardiac treatment and monitoring system which includes a defibrillator releasably coupled to a patient monitoring unit. The monitoring unit may be used to supply power to the defibrillator when it is operating on AC mains power, and also when operating on battery power if the monitor is equipped with an equal or greater number of user-exchangeable battery packs.

BRIEF DESCRIPTION OF THE DRAWINGS

FIG. 4 depicts the cardiac treatment unit and defibrillator of FIG. 1 in connection with a docking station.

DETAILED DESCRIPTION OF A PREFERRED EMBODIMENT

Figure 1:
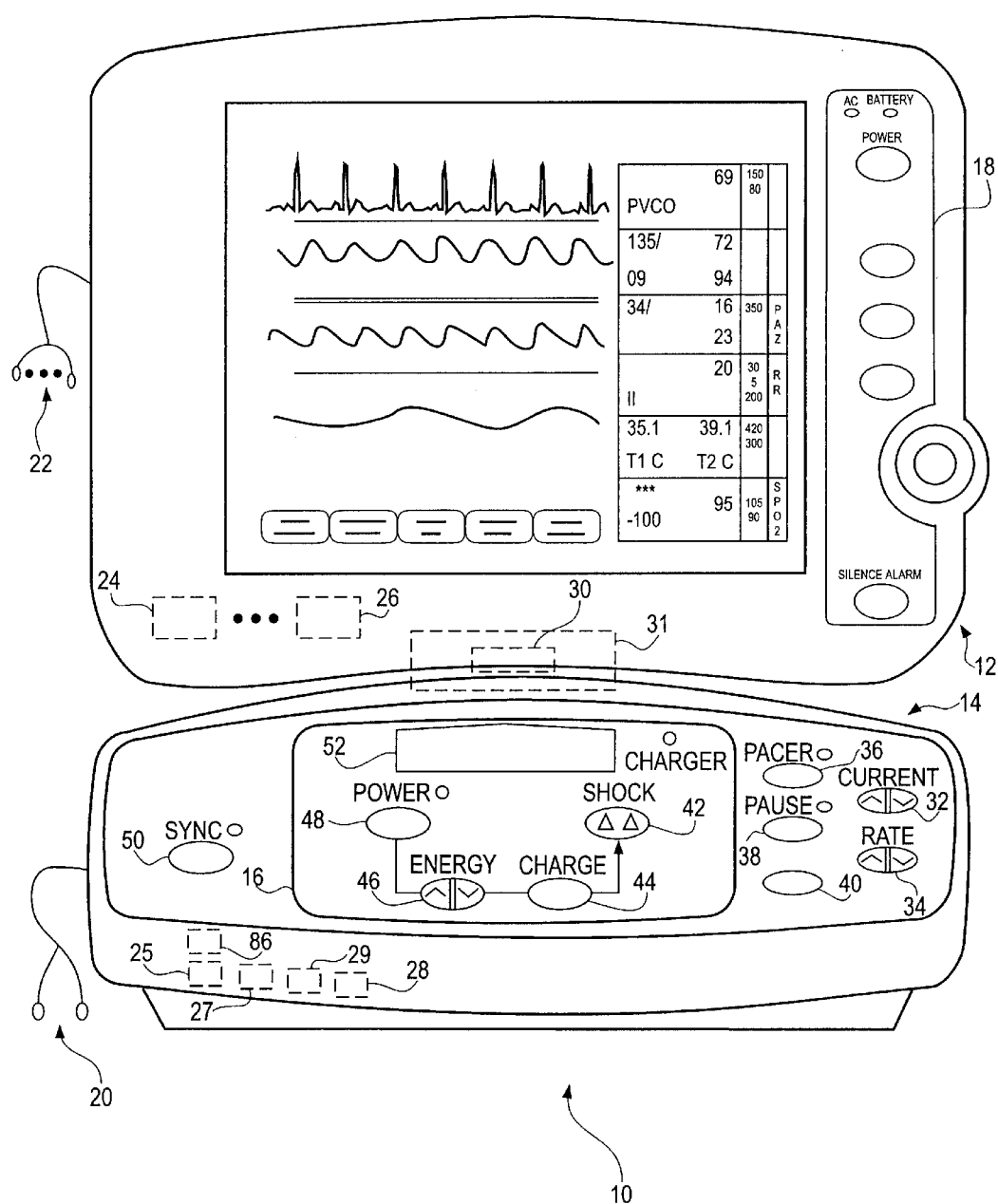
FIG. 1 is a front view of a cardiac treatment and monitoring system in accordance with an illustrated embodiment of the invention.

FIG. 1 depicts a cardiac treatment and monitoring system 10, shown generally under an illustrated embodiment of the invention. Included within the system 10 may be a defibrillation unit 14 and patient monitor 12.

Under illustrated embodiments of the invention, the patient monitor 12 may be releasably attached to the defibrillation unit 14. When detached, each device 12, 14 may be used separately. The defibrillator 14 may be equipped with its own internal power source (e.g., a battery) 28 and internal control system to allow stand-alone use. A control panel 16 may be provided for selection and control of defibrillation processes. A set of leads 20 may be provided to couple an output of the defibrillator to a body of a patient (not shown).

The leads 20 may be applied directly to the patient. One lead may be applied to the right front chest and the second lead to the left back of the patient.

For example, the operator (also not shown) may activate a power-on button 48. The operator may then activate a power up/down button 46 to select a power level (in Joules) for defibrillating the patient. A selected power level may be shown on a display 52.

Following selection of a power level, the operator may activate a charge button 44. Upon activation of the charge button 44, power from the battery 28 may flow through a voltage to voltage converter 86 and into a shock capacitor 27. By activating the shock button 42, the operator may trigger a switch 25, which applies a defibrillating shock through the leads 20 to the patient.

The patient monitor 12 may also be provided with its own internal power source (e.g., a battery) 24, 26 and internal control system to allow stand-alone use. A control panel 18 may be provided for selection and control of patient monitoring processes (e.g., electrocardiogram, blood pressure, $CO_2$, invasive pressure monitoring, blood temperature, cardiac output, blood oxygen saturation, etc.). A set of leads 22 may be provided which may be coupled to the patient for detection of parameters related to a particular patient monitoring process.

Interface between Monitor and Defibrillator A mechanical interface 31 is provided to secure and mount the patient monitor 12 to the defibrillator 14. An electrical interface (e.g., electrical connector set) 30 may also be provided to couple power and control signals between the monitor 12 and defibrillator 14.

Figure 2:
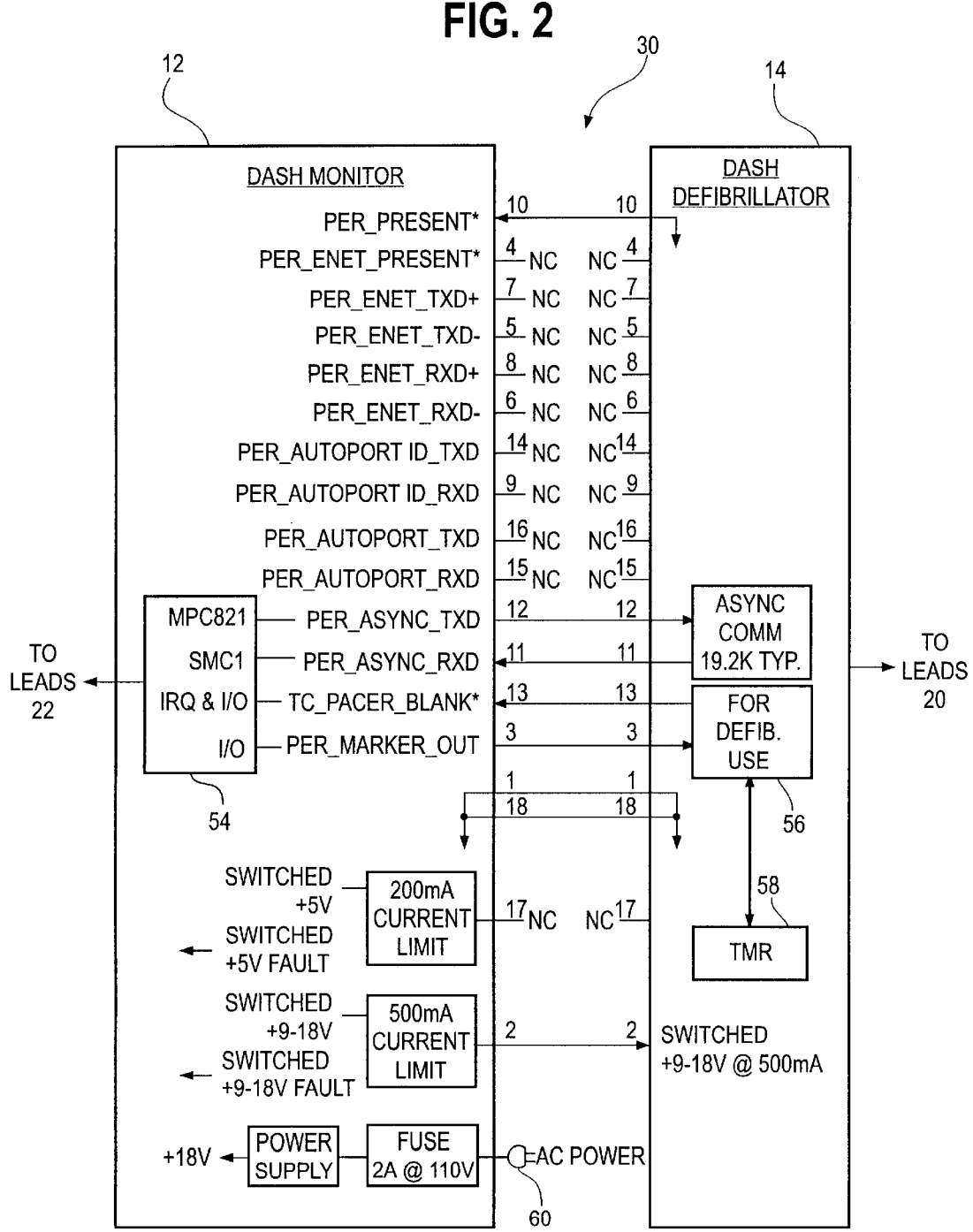
FIG. 2 is a schematic of a connection diagram that may be used to couple a patient monitoring unit of the cardiac treatment and monitoring system to a defibrillator of the cardiac treatment and monitoring system of FIG. 1.

FIG. 2 depicts a connection diagram showing electrical connections that may be established through the electrical connector set 30. Reference shall be made to FIG. 2 as appropriate to an understanding of the invention.

Under an illustrated embodiment of the invention, the leads 22 of the patient monitor 12 may be connected to an appropriate set of heart monitoring locations on the body of the patient. Using American Heart Association (AHA) lead naming convention, the leads may be connected to the left arm, right arm, left leg, right leg and chest.

A cardiac signal processor 54 may detect a QRS complex of the patient and, in response, generate an R-marker pulse. The R-marker pulse may be transmitted through the connector 30 (e.g., through connector terminal #3) to a defibrillator control CPU 56. Within the defibrillator 14, the R-marker may be used for defibrillator synchronization.

For example, where a pacer pushbutton 36 is activated, the defibrillator 14 may be used in a pace maker mode. A beat rate and current may be selected through pushbuttons 32, 34 and shown on display 52. A timer 58 within the defibrillator 14 may be used to provide a pacemaker pulse interval. A pulse generator 29 may be used to generate a pacing pulse.

Alternatively, the operator may activate a demand mode button 40. In the demand mode, the timer 58 is reset each time an R-marker is received from the patient monitor 12. However, if an R-marker is not received within a predetermined time period, the controller 56 triggers the pulse generator 29 thereby pacing the heart in the absence of a detected heartbeat.

It should be noted, in this regard, that for pacemaking and demand pacing, the pulse generator 29 bypasses the shock capacitor 27. Bypassing the shock capacitor 27 is possible because of the lower energy needs of pacemaking and demand pacing.

The connectors 30, 92 may be used to convey a number of control and information signals among the coupled devices. A first pin (e.g., pin 10) may provide indication of the presence of a connected peripheral device (PER_PRESENT). A second pin (e.g., pin 4) may provide indication of the presence of a peripheral network connection (PER_ENET_PRESENT). Similarly, a third pin (e.g., pin 7) may provide a non-inverted peripheral network transmit signal (PER_ENET_TXD+); a fourth pin (e.g., pin 5) may provide an inverted peripheral network transmit signal (PER_ENET_TXD−); a fifth pin (e.g., pin 8) may provide a non-inverted peripheral network receive signal (PER_ENET_RXD+); a sixth pin (e.g., pin 6) may provide an inverted peripheral network receive signal (PER_ENET_RXD−); a seventh pin (e.g., pin 14) may provide a peripheral communication channel number 1 device identifier transmit signal (PER_AUTOPORT_ID_TXD); a eighth pin (e.g., pin 9) may provide a peripheral communication channel number 1 device identifier receive signal (PER_AUTOPORT_ID_RXD); a ninth pin (e.g., pin 16) may provide a peripheral communication channel number 1 transmit signal (PER_AUTOPORT_TXD); a tenth pin (e.g., pin 15) may provide a peripheral communication channel number 1 receive signal (PER_AUTOPORT_RXD); an eleventh pin (e.g., pin 12) may provide a peripheral communication channel number 2 transmit signal (PER_ASYNC_TXD); a twelveth pin (e.g., pin 11) may provide a peripheral communication channel number 2 receive signal (PER_ASYN_RXD); a thirteenth pin (e.g., pin 13) may provide a pacer blanking signal (TC_PACER_BLANK); and a fourteenth pin (e.g., pin 3) may provide an Rmarker out signal (PER_MARKER_OUT).

The R-marker may also be used for synchronized cardioversion. As above, an energy level may be selected through the pushbutton 46 and display 52. Upon activation of the shock button 42, the controller 56 may delay application of the cardioversion shock through the leads 20 until detection of the next R-marker from the monitor 12.

Connector 30 includes a pacer blanking signal (TC_PACER_BLANK) from the defibrillator to the monitor to reject artifacts on the monitored ECG signal due to the pace pulse being applied to the patient.

To facilitate demand pacing and synchronized cardioversion, connector 30 provides bi-directional asynchronous communication signals for the exchange of control and status information between the monitor and the defibrillator (e.g., ECG lead quality, operating mode, etc.).

FIG. 4 depicts a docking station 90 that may be used with the patient monitoring unit 12 or defibrillator 14. The docking station 90 may be used for such things as connecting to a communication network, connecting to peripheral devices or providing power to the monitor.

Included on the defibrillator 14 may be first and second connectors. As shown, the first connector 30 may be used to releasably couple the patient monitoring unit 12 to the defibrillator 14. The second connector 92 may be used to releasably couple the defibrillator 14 to the docking station 90.

Alternatively, the defibrillator 14 may be provided with complementary connectors 30, 92. For example, if the patient monitor 12 has a female connector 30 and the defibrillator has a male connector 30, then the docking station may also be provided with a male connector 30. Where provided with complementary connectors 90, the docking station 92 may be coupled to either the patient monitor unit 12 or the defibrillator 14.

To facilitate use of the docking station 90 with either the patient monitor 12 or defibrillator, connectors 30, 92 may be provided with identification features to identify a connected device. For example, when the patient monitoring unit 12 is coupled to the defibrillator 14, a grounded pin #10 alerts the patient monitoring unit 12 to the presence of a connected device. The patient monitoring unit 12 may then transfer an identity request over a transmit port #12 and monitor a receive port #11 for an identifier. Alternatively, the patient monitoring unit 12 may transmit an identify request over ENET pins #5,7 and monitor ENET pins #6, 8 for a response.

The same mechanical coupling that is used to detachably couple the monitor and defibrillator may be used to detachably couple the monitor to the docking station. The mechanical coupling has two complementary mating parts. The defibrillator may be constructed with one of each type of mating part on the top and bottom, respectively. The docking station may be constructed with both types in a side-by-side relationship to allow any docking combination.

Power Distribution

Figure 3:
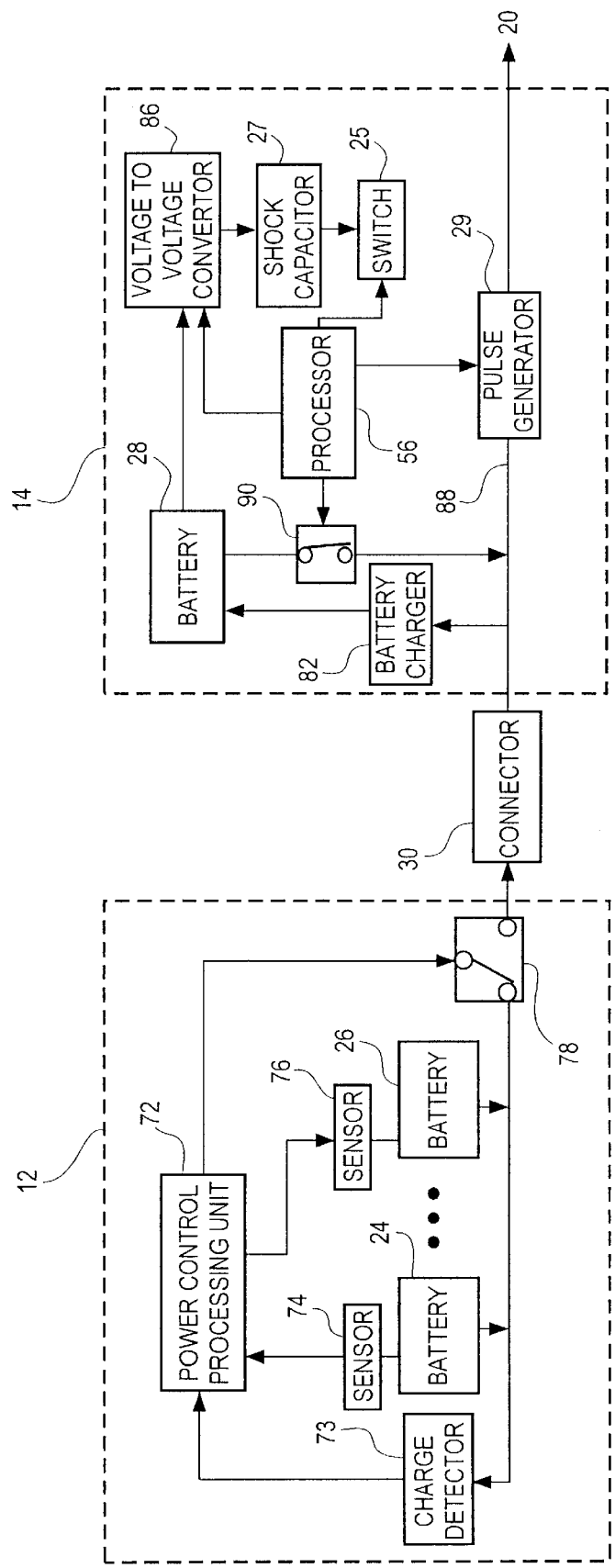
FIG. 3 depicts a power distribution system used by the system of FIG. 1.

FIG. 3 depicts a power distribution system 70 that may be used by the system 10 of FIG. 1. Under illustrated embodiments of the invention, the monitor 12 conditionally shares power with the defibrillator 14. As is known, defibrillators typically require a battery technology (e.g., NiCd, lead-acid, etc.) which is capable of rapidly charging the shock capacitor 27. However, NiCd or lead-acid batteries have a very poor energy density. Further, in life threatening situations, it is considered better to have a monitor 12 with a dead battery than a defibrillator 14 with a dead battery.

In general, the defibrillator 14 uses power from the attached monitor 12 in preference to its own power to the greatest extent possible in order to conserve the energy within its own battery 28. Power from the monitor may be used to perform all defibrillator functions other than charging the shock capacitor 27. These functions include (but are not limited to) powering the processor, user interface, pacemaker, and battery charger 82. The pulse generator 29 under control of the CPU 56 functions to raise a voltage of a power supply main 88 to an appropriate level for pacing, cardioversion, etc.

If the monitor 12 is not present or fails to deliver the necessary power, the defibrillator battery 28 will operate the entire defibrillator 14. In this case, power steering diodes or the CPU 56 may activate switch 90 to supply power to the supply bus 88 and to the pulse generator 29. Alternatively, the CPU 56 may activate the voltage-to-voltage converter 86. Activation of the converter 86 charges the shock capacitor 27. Once the shock capacitor 27 is charged, the PCPU 80 may deliver the charge upon activation of the shock button 42 by activation of the switch 25.

The monitor 12 may have built-in or one or more exchangeable battery packs 24, 26. When the monitor 12 is operating on AC mains power from a plug 60 (FIG. 2), it supplies direct current (dc) power to the defibrillator 14 (FIGS. 2 and 3). When operating in the absence of AC mains power (i.e., on battery power), the monitor 12 makes power available to the attached defibrillator 14 as follows. Under one illustrated embodiment, if the monitor 12 is capable of operating from an equal or greater number of exchangeable battery packs 24, 26 than the defibrillator 14, then the monitor 12 supplies power to the defibrillator 14. Conversely, if the monitor 12 is capable of operating from fewer exchangeable battery packs 28 than the defibrillator 14, then the monitor 12 may not supply power to the defibrillator 14.

To monitor battery capacity in the monitor 12, a power control processing unit (PCPU) 72 (functioning as a battery reserve capacity analyzer) may monitor battery reserve capacity under any one of a number of formats. For example, battery reserve may be determined by the number of connected batteries or by the charge level of the connected batteries.

For example, the PCPU 72 may monitor for the presence of battery packs 24, 26 through the use of sensors (e.g., limit switches, proximity detectors, etc.) 74, 76. A charge detector 73 may monitor a charge level of the batteries 24, 26 based upon voltage. Based upon the reserve capacity of the monitor (e.g., greater than 50%) and the number of batteries 24, 26 detected by sensors 74, 76, the PCPU 72 may operate a switch 78 to conditionally supply power to the defibrillator 14.

Similarly, the defibrillator 14 may consume power under control of a CPU 56. If situations where charging of the shock capacitor 27 is required, the CPU 56, under control of the switch 44, may cause the converter 86 to become active.

Activation of the converter 86 causes the battery 28 to charge the shock capacitor 27.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A cardiac treatment and monitoring system comprising:
   a patient analyzer unit adapted to detect and analyze processes occurring within a body of a patient;
   a defibrillator unit releasably coupled to the patient analyzer unit and adapted to receive information about the detected and analyzed processes from the patient analyzer; and
   a power distribution system disposed within the patient analyzer unit and adapted to conditionally share power from a power source of the patient analyzer with the defibrillator.

2. The cardiac treatment and monitoring system as in claim 1 wherein the power source further comprising a plurality of batteries.

3. The cardiac treatment and monitoring system as in claim 2 wherein the power distribution system further comprises a battery capacity analyzer adapted to determine a battery capacity of the patient analyzer unit.

4. The cardiac treatment and monitoring system as in claim 3 wherein the battery capacity analyzer further comprises a battery sensor adapted to detect a battery of the plurality of batteries coupled to a battery connection of the patient analyzer unit.

5. The cardiac treatment and monitoring system as in claim 3 wherein the battery capacity analyzer further comprises a battery charge level detector coupled to a power bus of the power distribution system.

6. The cardiac treatment and monitoring system as in claim 2, further comprising a power switch disposed within the patient analyzer unit and adapted to couple power from the plurality of batteries to the defibrillator unit when the battery capacity analyzer determines that a reserve capacity of the plurality of batteries exceeds a threshold, value.

7. A method of distributing power within a cardiac treatment and monitoring system which includes a defibrillator releasably coupled to a patient monitoring unit, such method comprising the steps of:
   determining a battery reserve capacity within the patient monitoring unit; and
   distributing power from the patient monitoring unit to the releasably coupled defibrillator when the determined battery reserve capacity exceeds a threshold value.

8. The method of distributing power as in claim 7 wherein the step of determining a battery reserve capacity further comprises determining a number of batteries coupled to the patient monitoring unit.

9. The method of distributing power as in claim 8 wherein the step of determining a battery reserve capacity further comprises determining that the number of batteries coupled to the patient monitoring unit exceeds a number of batteries coupled to the defibrillator.

10. The method of distributing power as in claim 8 wherein the step of determining a battery reserve capacity further comprises determining a charge reserve capacity remaining within batteries coupled to the patient monitoring unit.

11. The method of distributing power as in claim 7 further comprising providing power to the,defibrillator from an alternating power source.

12. The method of_distributing power as in claim 7 further comprising powering the defibrillator from a defibrillator battery during charging of a shock capacitor of the defibrillator.

13. The method of distributing power as in claim 7 further comprising powering a battery charger within the defibrillator for charging a defibrillator battery.

14. An apparatus for distributing power within a cardiac treatment and monitoring system which includes a defibrillator releasably coupled to a patient monitoring unit, such apparatus comprising:
   means for determining a battery reserve capacity within a patient monitoring unit; and
   means for distributing power to from the patient monitoring unit to the releasably coupled defibrillator when the determined battery reserve capacity exceeds a threshold value.

15. The apparatus for distributing power as in claim 14 wherein the means for determining a battery reserve capacity further comprises means for determining a number of batteries coupled to the patient monitoring unit.

16. The apparatus for distributing power as in claim 15 wherein the means for determining a battery reserve capacity further comprises means for determining the number of batteries coupled to the patient monitoring unit that exceeds a number of batteries coupled to the defibrillator.

17. The apparatus for distributing power as in claim 15 wherein the means for determining a battery reserve capacity further comprises means for determining a charge reserve capacity remaining within batteries coupled to the patient monitoring unit.

18. The apparatus for distributing power as in claim 14 further comprising means for providing power to the defibrillator from an alternating power source.

19. The apparatus for distributing power as in claim 14 further comprising means for powering the defibrillator from a defibrillator battery during charging of a shock capacitor of the defibrillator.

20. The apparatus for distributing power as in claim 14 further comprising means for powering a battery charger within the defibrillator for charging a defibrillator battery.

21. An apparatus for distributing power within a cardiac treatment and monitoring system which includes a defibrillator releasably coupled to a patient monitoring unit, such apparatus comprising:

a battery reserve capacity analyzer adapted to determine a battery reserve capacity within the patient monitoring unit; and a power distribution system adapted to distribute power from the patient monitoring unit to the releasably coupled defibrillator when the determined battery reserve capacity exceeds a threshold value.

22. The apparatus for distributing power as in claim 21 wherein the battery reserve capacity analyzer further comprises a plurality of battery sensors adapted to alert the battery reserve capacity analyzer when a battery is coupled to the patient monitoring unit.

23. A cardiac treatment and monitoring system comprising:

a cardiac analyzer unit adapted to detect and analyze a QRS complex of a patient;

a defibrillator unit releasably coupled to the cardiac analyzer unit and adapted to receive QRS information of the analyzed QRS complex from the cardiac analyzer unit; and a power distribution system disposed within the cardiac analyzer unit and adapted to conditionally share power from a power source of the cardiac analyzer unit with the releasably coupled defibrillator unit.

* * * * *